United States Patent [19]

Lustig

[11] 4,276,027
[45] Jun. 30, 1981

[54] PARAPULPAL DENTAL RESTORATIVE PINS WITH SELF-ANCHORING ANTI-ROTATIONAL RETENTION HEADS

[76] Inventor: Leopold P. Lustig, 304 Greenwood St., Newton Centre, Mass. 02159

[21] Appl. No.: 100,942

[22] Filed: Dec. 6, 1979

[51] Int. Cl.³ .............................................. A61C 5/04
[52] U.S. Cl. .................................................... 433/225
[58] Field of Search ................. 433/225, 220; 24/73 P, 24/73 PM; 85/7, 5 R

[56] References Cited

U.S. PATENT DOCUMENTS

| | | | |
|---|---|---|---|
| 2,438,725 | 3/1948 | Tamarin | 433/225 |
| 3,272,059 | 9/1966 | Lyday et al. | 24/73 PM |
| 3,473,223 | 10/1969 | Karlstrom | 433/220 |
| 3,530,584 | 9/1970 | Karlstrom | 433/225 |

FOREIGN PATENT DOCUMENTS

| | | | |
|---|---|---|---|
| 1140690 | 8/1957 | France | 433/220 |
| 548228 | 12/1929 | Fed. Rep. of Germany | 433/220 |

*Primary Examiner*—Robert Peshock
*Attorney, Agent, or Firm*—Alfred H. Rosen

[57] ABSTRACT

Parapulpal dental restorative pins for use with all forms of dental restorative materials, including impression-taking materials, modeling waxes and the like, as well as amalgams, gold and other materials used for constructing a superstructure on a natural tooth, have heads to anchor the pins in such materials, and means on the head to prevent the head from rotating around the longitudinal axis of the pin in the restorative material. A constricted neck between the head and the principal body of the pin allows the head to be oriented into a plane that is not perpendicular to the pin axis. The heads can take various shapes and configurations. A composite pin, having a principal body made of one material and a head made of another is shown.

11 Claims, 12 Drawing Figures

PARAPULPAL DENTAL RESTORATIVE PINS WITH SELF-ANCHORING ANTI-ROTATIONAL RETENTION HEADS

BACKGROUND OF THE INVENTION

This invention relates to parapulpal dental restorative pins in general, including pins used for taking impressions and making models, as well as pins used for securing restorative materials directly to a tooth understructure. More particularly, the invention relates to a parapulpal dental restorative pins with self-anchoring anti-rotation retention heads, and is applicable to pins of all forms, whether threaded or non-threaded.

Screw-threaded pins for securing dental fillings are disclosed in U.S. Pat. No. 114,454 of Mack and No. 143,418 of Osmond. These early pins were made of metallic wire, gold being mentioned in Osmond. Mack's pin had no head, although he mentions but does not show pins with flattened heads. He simply packed the filling about the pins. Osmond shows a pin with one end split. He packs filling material around the pin to form a base, and then opens the split end of the pin over the base, after which the balance of the filling is made over the base and the opened parts of the split end. He can alternatively open the split end of the pin first, and then pack the filling around it.

This early recognition of a need to retain fillings secured on screw pins from displacement axially along the pins persisted for many years, and is again recognized in U.S. Pat. No. 3,675,329 of Weissman. In a screw pin structure directed primarily to a manipulating portion which is severable, Weissman includes a rounded flanged head for enhancing the resistance against axial displacement of a superstructure relative to the understructure of a tooth.

The prior art includes other forms of pins for anchoring a superstructure or restoration to a tooth. There are, for example, non-threaded pins having a diameter slightly smaller than the hole into which it will be secured, in which case a suitable cement (with which the present invention is not concerned) is used to hold the pin in place. In another form of non-threaded pin, the pin has about the same diameter as that of the hole, and the pin is force-fitted or friction-locked into the hole, to hold the pin in place.

GENERAL NATURE OF THE INVENTION

The present invention is applicable to not only anchoring pins of all types but also to pins for all purposes, including without limitation, the taking of impressions and the making of models. Parapulpal dental restorative pins according to the invention have a head which is stabilized against rotation around the axis of the pin, so that whatever the material in which it is imbedded, the pin will be held in that material stably against rotation around its axis as well as against displacement along the pin axis. This is as important when an impression-taking pin is imbedded in a delicate impression-taking material such as a hydrocolloid, or in a wax-up material, to assure precision in the casting of a crown or bridge, as it is for retaining a superstructure that is built up around a pin or pins on a natural-tooth understructure. It also makes possible the reliable use of parapulpal dental reconstruction pins with heads that can be bent relative to the longitudinal axis of the pin, to conform with the contour of the understructure while maintaining parallelism among several pins in an impression-taking material. Here the assurance against rotation around the pin axis is critical to holding the axes of several pins in parallelism for ultimate transfer to a cast reconstruction. The invention according includes means providing a readily-bendable constricted neck between the head and the principal body of the pin, for permitting the head to be oriented into a plane that is not perpendicular to the longitudinal axis of the pin.

Self-anchoring anti-rotational heads for parapulpal dental reconstruction pins according to the invention can take a wide variety of shapes and forms. A simple form has a slot running from the periphery axially inward to the pin, for receiving some of the material in which the pin is embedded. The head can be round or not round, a simple rectangular form with radial slot being illustrated as one preferred embodiment that is not difficult to make. An alternative form is a simple round head that has been chordally flattened in one or more locations. Such a head chordally-flattened in two diametrically-opposite locations can approximate a rectangle; if flattened in three places it can approximate a triangle. Bearing in mind, however, the small sizes of parapulpal dental reconstruction pins, the heads will have maximum transverse dimensions of about 1 millimeter, as compared with a pin diameter of about 0.5 millimeter or less. At these small sizes, anti-rotational designs of cruciform shapes, or multi-slotted forms, may be preferred for some uses.

DESCRIPTION OF THE INVENTION

Figure 1:
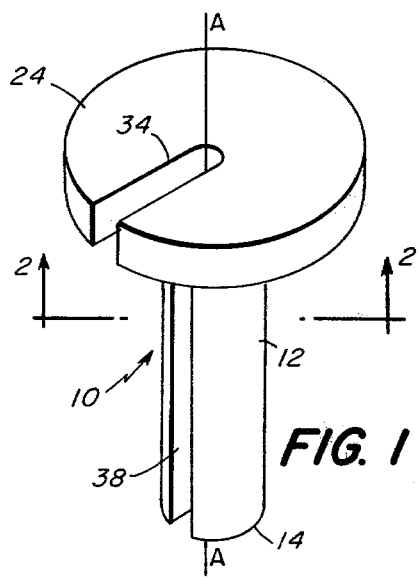
FIG. 1 illustrates the general features of a parapulpal dental restorative pin according to the invention.
Figure 2:
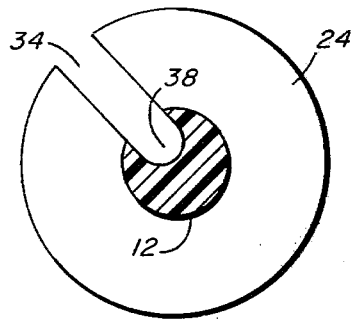
FIG. 2 is a section on line 2—2 of FIG. 1.
Figure 3:
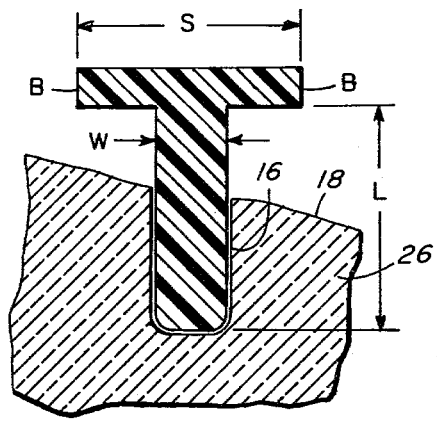
FIG. 3 is a partial section illustrating features of the pin of FIG. 1 in use.

FIGS. 1 to 3 inclusive illustrates the general features of a parapulpal dental restorative pin 10 according to the invention. The pin has a principal body 12 which is elongated on an axis A—A to form a pin intended for insertion at one end 14 into a hole 16 through a surface 18 and when so inserted to extend at the other end 22 a distance from the surface. A head 24 that is flattened to embrace a plane B—B transverse to the axis A—A is fixed to the other end 22 of the principal body 12. The head 24 is adjacent to but spaced from the surface 18 when the pin is so inserted in the hole 16.

Figure 1A:
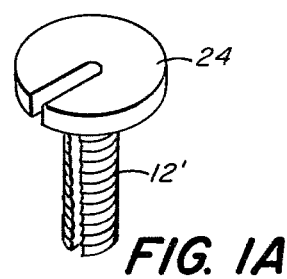
FIG. 1A shows a variation of the pin shown in FIG. 1.

The hole 16 is formed in a material 26 which is representative of parapulpal dentin which has been prepared for reconstruction on the surface 18, or a model of such a tooth on which, for example, a wax-up or model of other suitable modelling material is to be made. The pin 10 can be smooth as shown, and can be made of a wide variety of materials (e.g: plastics, metals, ceramics, or combinations of these or other suitable materials), a plastics material being indicated in the drawings as might be chosen for taking impressions and making a wax-up. However, threaded pins, as shown in FIG. 1A, having screw threads on the principal body 12', are within the ambit of the invention. The free end or tip 14 in any case is preferably rounded, as will be described.

For taking an impression a smooth plastic pin as illustrated in FIG. 3 can be used. The impression material (not shown) will flow around and under the head 24, and when the impression material sets the pin will come out of the hole 16 when the impression is separated from the tooth 25. The pin can then be used with the impression to make a model reproducing the contours of the surface 18 and the hole 16. On the other hand, a retention pin, for example, a screw pin as shown in FIG. 1A, made of a suitable metal such as gold, would be used for building a restoration in place out of amalgam, gold or other suitable material. The restoration material would, again, be formed around and under the head 24, for retention purposes.

The head 24 is provided with means, represented in FIGS. 1-3 by a notch 34 extending radially inward from the periphery of the head, to prevent the head 24 from rotating around the axis A—A within the modeling or restoration material. This assures precision in fabricating the dental restoration, and stability after completing the restoration. A groove 38 extends axially along one side of the principal body 12, into substantial register with the bottom of the notch 34, for venting the hole 16 when the pin is inserted into it. This groove meets the rounded tip 14.

It will be seen that when the pin is inserted in the hole 16 the plane B—B of the head 24 may not be parallel to the surface 18. FIGS. 4-8 show pin structures according to the invention which incorporate a readily bendable constricted neck 40 joining the head to the principal body, for permitting the head to be oriented into a plane that is not perpendicular to the axis A—A. This allows the head to be adjusted relative to the surface 18 before or after the pin has been inserted into the hole 16. In general, the neck is thinner than the width dimension of the principal body, as can be seen in any of FIGS. 4, 6 and 7.

Figure 4:
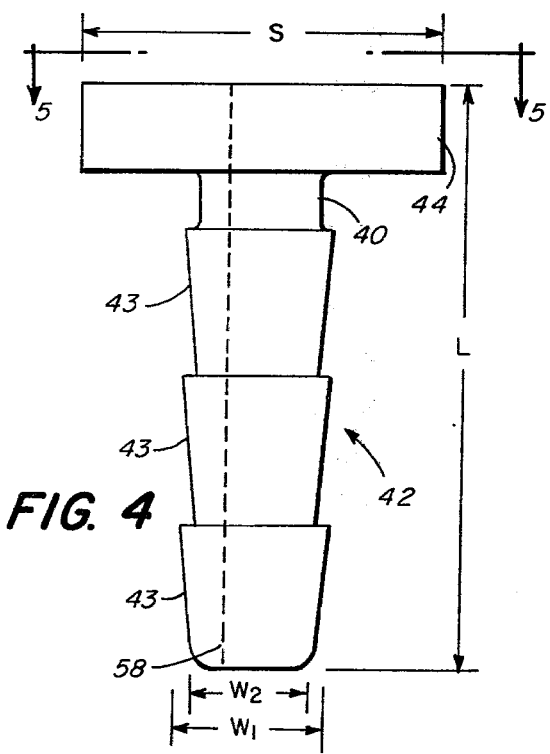
FIG. 4 is a side view of another dental restorative pin of the invention.
Figure 5:
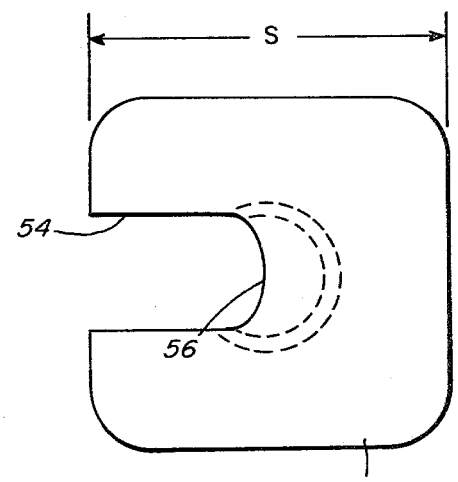
FIG. 5 is a view taken on line 5—5 of the pin in FIG. 4.
Figure 6:
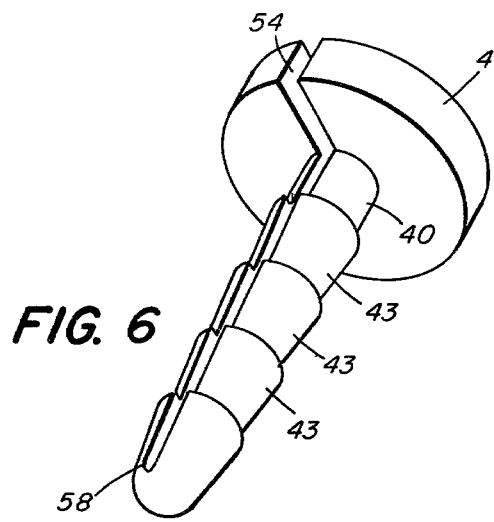
FIG. 6 is an isometric view of a pin like that shown in FIGS. 4 and 5.

FIGS. 4-6 illustrate a retention pin intended for permanent installation, hence preferably made of a precious metal such as gold or an iridio-platinum alloy. The principal body 42 has a series of axially limited tapered regions 43 in each of which the width of the principal body is tapered from the major transverse dimension down to a minor transverse dimension. The tapered regions extend end-to-end, the narrow end of each region abutting the wide end of the next succeeding region, the wide ends oriented toward the head 44, for retaining the pin in a bonding material, not shown, when the pin is inserted in a hole such as the hole 16 with such a bonding material.

The head 44 is rectangular as shown in FIG. 5, but it can have another shape; it can be round as shown in FIG. 6. A notch 54 extends from the periphery of the head inward to the principal body 42, where a groove 58 extending axially along one side of the principal body meets the bottom 56 of the notch.

Figure 7:
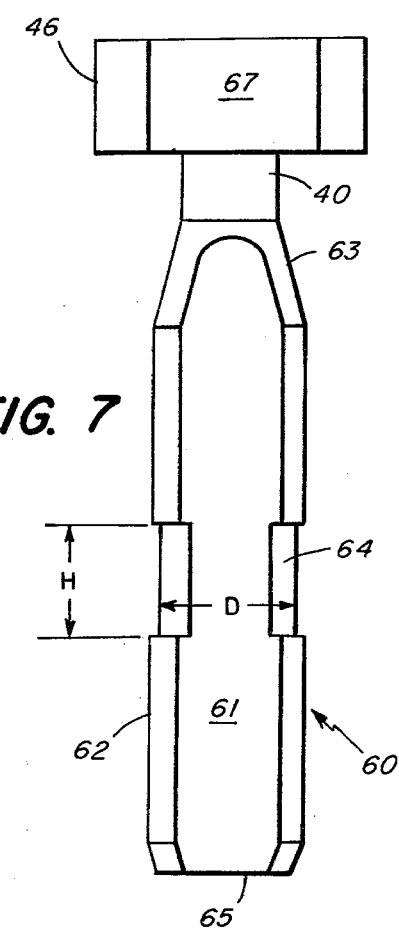
FIG. 7 is a side view of another dental reconstruction pin of the invention.
Figure 8:
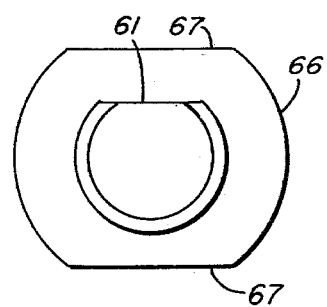
FIG. 8 is a transverse section taken on line 8—8 of FIG. 7.

FIGS. 7 and 8 show a pin 60 which can be used for temporization as well as longer duration dental restorations. This pin is intended to hold temporary restorations, and is provided with retention capability which can be intentionally defeated by the dentist so that a temporary restoration can be removed when that is desired. The principal body 62 is generally cylindrical, and chordally-flattened along one side 61 for venting the hole (e.g: hole 16) into which the pin is inserted. A short tapered section 63 connects the neck 40 to the principal body 62 at one end. An intermediate region 64 of limited axial length H is reduced in diameter to a minor transverse dimension D, to provide a substantially annular pocket between the transition section 63 and the free end 65, for retaining a bonding material, when the pin is inserted into a hole with such a bonding material. Two or more such axially-limited regions can be provided, if desired. The head 66 has two chordally-flattened sections 67,67 on opposite sides, to prevent rotation within a restorative material (not shown) around the axis A—A of the principal body. For a temporary restoration pins as shown in FIGS. 7 and 8 can be made of a non-precious metal, such as aluminum. They can also be made of other materials such as precious metals, or plastics for example, if intended for other uses.

Figures 9, 10:
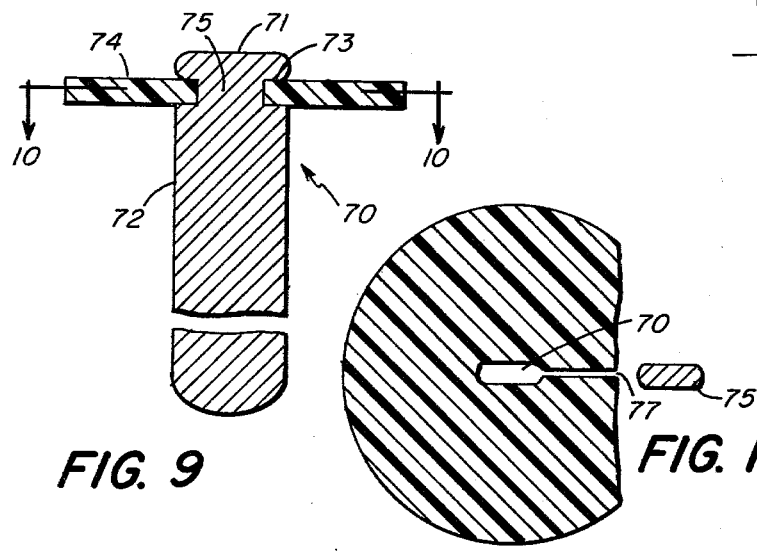
FIG. 9 is a longitudinal section through a composite parapulpal dental reconstruction pin according to the invention.
FIG. 10 is a partial section on line 10—10 of FIG. 9 showing how the parts are assembled.
Figure 11:
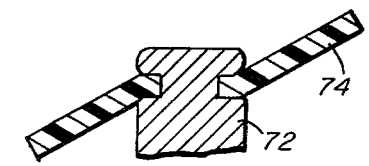
FIG. 11 shows a feature of the composite pin in FIG. 9.

FIGS. 9 to 11, inclusive, illustrate a composite pin 70 having a principal body 72 made of metal, and a head 74 made of a plastics material. The principal body can take any desired form, for example as in FIG. 6, or in FIG. 7; it is illustrated without any particular form in FIGS. 9-11. At the top 71 end the principal body has a groove 73 around a stem 75 which has a rectangular cross-section shown in FIG. 10. The head has a matching hole 76 connecting to the outer periphery via a slot 77. The head is assembled to the principal body by forcing the stem 75 through the slot 77 into the hole 76. When the two parts 72,74 are assembled into a unitary article of manufacture, the head 74 will not rotate around the axis of the principal body, and the slot 77 will be useful to prevent the head from rotating within a reconstruction material, like the notch 34 in FIG. 1, for example. The head 74 can be tilted relative to the axis of the principal body 72 by heating it and forcing it while plastic into a tilted position, as is shown in FIG. 11.

In preparing a cast-metal restoration, a composite pin can be placed in a wax-up, and the head 74 will combust with the wax, after which the principal body 72 of the pin will be fixed in the casting. A dental restorative metal principal body, similar to those shown in FIGS. 4-8, is preferable for that purpose. Alternatively the head 74 can be made of a material that is suitable for cosmetic restoration purposes, such as an acrylic, composite resin, porcelain, or the like, in which case the restoration is built up around the head out of a like restoration material on the tooth to be restored. Being of similar material the cosmetic head will not show through a thin, translucent dental restorative layer.

Figure 12:
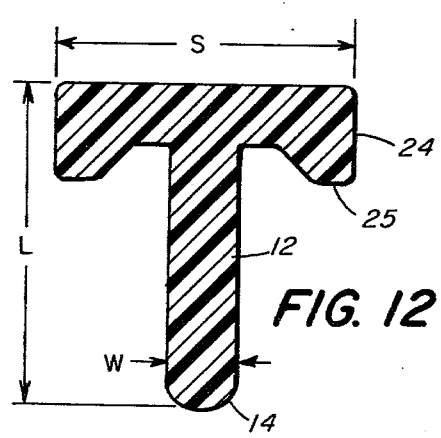
FIG. 12 shows an embodiment of the invention suitable for certain special purposes.

In FIG. 12 a pin suitable for impressions and wax-ups is similar to the pin shown in FIGS. 1-3, and like parts bear like reference numbers. The head 24 includes a skirt 25 which extends toward the free end 14 of the principal body 12. The head 24 and the skirt 25 have rounded edges when intended for taking impressions, in order to avoid imposing unsuitable stresses on impression materials such as hydrocalloids. For use in making wax-ups, for example, these edges can be squared. In use, when the pin is inserted into a hole, such as the hole 16 in FIG. 3, the skirt will extend toward the surface 18 through which the hole extends. The skirt is useful to retain soft impression materials and wax-up materials under the head 24.

As is seen in FIGS. 3, 6 and 12, the free end 14, or 58, of the pin is preferably rounded. This structural feature helps to prevent creating undue stress on dentin during insertion of screw pins in holes 16 prepared in a natural tooth. During cementation, it helps to prevent expulsion of the pin caused by hydraulic pressure due to viscosity of dental cements in the semi-set stage.

I claim:

1. A dental restorative pin comprising a metallic principal body that is elongated on an axis forming a pin intended for insertion at one end into a hole through a surface and when so inserted to extend at the other end a distance from said surface, and at said other end a head that is flattened to embrace a plane transverse to said axis, in which said head will be disposed adjacent to but spaced from said surface when said pin is so inserted, for engaging said head in a dental restorative material when the latter is present on said surface, said head being joined to said other end of said principal body by a constricted neck located immediately between said other end and said head, said neck being thinner than the width dimension of said principal body and extending axially a small fraction of the length of said principal body, for permitting said head to be oriented around said other end relative to said axis into a plane that is not perpendicular to said axis, for adjusting said head relative to said surface when said pin is so inserted in said hole, a notch in said head extending from the periphery of said head to said principal body, and means providing a passage extending axially along one side of said principal body into substantial register with the bottom of said notch, whereby when said pin is inserted into said hole, said hole will be readily vented without displacing dental restorative material from under said head, the width of said principal body being tapered from the major transverse dimension down to a minor transverse dimension in each of a plurality of axially-limited regions extending end-to-end from said one end to said other end of said principal body, the narrow end of each said region abutting the wide end of the next succeeding region, the wide ends of said regions being oriented toward said head, for retaining said pin in a bonding material when said pin is inserted in said hole with said bonding material.

2. A dental restorative pin according to claim 1 in which said one end is substantially rounded.

3. A dental restorative pin according to claim 1 in which said head is substantially non-circular in shape.

4. A dental restorative pin according to claim 1 in which said head has a notch extending from the periphery to said principal body, and in which said principal body has a groove extending axially along one side into substantial register with the bottom of said notch.

5. A dental restorative pin according to claim 1 in which said head has a skirt extending from its periphery toward but not reaching said surface when said pin is so inserted in said hole.

6. A dental restorative pin according to claim 1 in which the width of said principal body is tapered from said major width dimension to the width of said neck in a transition region which extends axially a minor fraction of the length of said principal body.

7. A dental restorative pin according to claim 6 in which the width of said principal body is reduced to a minor transverse dimension in at least one limited region located between said transition region and the free end of said principal body, to provide a substantially annular pocket for retaining a bonding material when said pin is so inserted in said hole.

8. A dental restorative pin according to claim 1 in which said principal body is generally cylindrical with its width dimension reduced in a restricted angular region extending axially along a side of said body.

9. A dental restorative pin according to claim 8 in which said principal body is chordally flattened in said restricted angular region.

10. A dental restorative pin according to claim 8 in which said principal body has a groove extending along said side in said restricted angular region.

11. A unitary article of manufacture according to claim 1 comprising a principal body made of a metal and having at said other end a head which is made of a non-metallic material selected from plastics and cosmetically-compatible dental restorative materials, said head being affixed non-rotatively to said pin.

* * * * *